(12) United States Patent
Peters et al.

(10) Patent No.: US 6,884,807 B2
(45) Date of Patent: Apr. 26, 2005

(54) 3-SUBSTITUTED QUINUCLIDINES AND THEIR USE AS NICOTINIC AGONISTS

(75) Inventors: Dan Peters, Malmö (SE); Gunnar M. Olsen, Frederiksberg (DK); Elsebet Østergaard Nielsen, København (DK); Philip K. Ahring, Bagsværd (DK); Tino Dyhring Jørgensen, Solrød Strand (DK)

(73) Assignee: Neurosearch, A/S, Ballerup (DE)

( * ) Notice: Subject to any disclaimer, the term of this patent is extended or adjusted under 35 U.S.C. 154(b) by 0 days.

(21) Appl. No.: 10/416,268

(22) PCT Filed: Nov. 28, 2001

(86) PCT No.: PCT/DK01/00791

§ 371 (c)(1),
(2), (4) Date: May 9, 2003

(87) PCT Pub. No.: WO02/44176

PCT Pub. Date: Jun. 6, 2002

(65) Prior Publication Data

US 2004/0044026 A1 Mar. 4, 2004

(30) Foreign Application Priority Data

Dec. 1, 2000 (DK) ........................................ 2000 01813
Mar. 5, 2001 (DK) ........................................ 2001 00352

(51) Int. Cl.[7] .................. A61K 31/439; A61K 31/4745; C07D 453/02; C07D 453/04; A61P 25/00
(52) U.S. Cl. ........................ 514/305; 546/133; 546/135; 546/114; 514/301; 514/302
(58) Field of Search ........................... 546/133; 514/305

(56) References Cited

U.S. PATENT DOCUMENTS

| | | | |
|---|---|---|---|
| 4,959,367 A | 9/1990 | King | |
| 5,177,084 A | 1/1993 | Baker et al. | |
| 5,227,386 A | 7/1993 | Böttcher et al. | |
| 5,491,148 A | 2/1996 | Berger et al. | |

OTHER PUBLICATIONS

Sterling et al. Journal of Pharmaceutical Science. 1991, 80(8): 785–789.*
Holladay et al. J. Med. Chem. 1997, 40(26):4169–4188.*
Levin et al. Psychopharmacology. 1998, 138(3–4): 217–30.*
Johansson, Gary, et al. J. Med. Chem., vol. 40, pp. 3804–3819, 1997.
Database STN International. File Caplus, Caplus; accession No. 1974:82740, document No. 80:82740, Mikhlina, E. E., et al. vol. 7, No. 12, pp. 23–26, 1973.
Nilsson, B. M. et al. J. Med. Chem, vol. 38, pp. 473–487, 1995.
Nordvall, Gunnar, et al. J. Med. Chem, vol. 39, pp. 3269–3277, 1996.
Clark, R.D., et al. J. Med. Chem. vol. 36, pp. 2645–2657, 1993.

* cited by examiner

*Primary Examiner*—Evelyn Mei Huang
(74) *Attorney, Agent, or Firm*—Birch, Stewart, Kolasch & Birch, LLP

(57) ABSTRACT

This invention relates to novel 3-substituted quinuclidine derivatives, which are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

4 Claims, No Drawings

3-SUBSTITUTED QUINUCLIDINES AND THEIR USE AS NICOTINIC AGONISTS

This application is the national phase under 35 U.S.C. §371 of PCT International Application No. PCT/DK01/00791 which has an International filing date of Nov. 28, 2001, which designated the United States of America.

TECHNICAL FIELD

This invention relates to novel 3-substituted quinuclidine derivatives, which are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exerts its biological effect via two types of cholinergic receptors, the muscarinic Acetyl Choline Receptors (mAChR) and the nicotinic Acetyl Choline Receptors (nAChR).

It is well established that muscarinic acetylcholine receptors are of importance in relation to memory and cognition, and much research aimed at the development of agents for the treatment of memory related disorders have focused on the synthesis of muscarinic acetylcholine receptor modulators.

Nilsson et al [Nelsson BM, Sundquist S, Johansson G, Nordvall G, Glas G, Nilvebrant L & Hacksell U; *J. Med. Chem.* 1995 38 473–487] describe the synthesis and muscarinic activity of certain 3-heteroaryl substituted quinuclidin-2-ene derivatives including 3-(2-benzofuranyl)quinuclidine-2-ene, 3-(3-benzofuranyl)quinuclidine-2-ene, 3-(2-benzothienyl)quinuclidine-2-ene, 3-(3-benzothienyl)quinuclidine-2-ene, 3-(2-benzoxazolyl)quinuclidine-2-ene, 3-(2-benzthiazolyl)quinuclidine-2-ene, 3-(2-benzofuranyl)-quinuclidine and 3-(2,3-dihydrobenzofuran-2-yl)quinuclidine.

Nordvall et al. [Nordvall G, Sundquist S, Johansson G, Glas G, Nilvebrant L & Hacksell U; *J. Med. Chem.* 1996 39 3269–3277] describe the synthesis and muscarinic activity of certain quinuclidine-2-ene derivatives including 3-(2-benzofuranyl)-quinuclidine-2-ene and 3-(2-furo[3,2-b]pyridinyl)quinuclidine-2-ene.

Johansson et al. [Johansson G, Sundquist S, Nordvall G, Nilsson B M, Brisander M, Nilvebrant L & Hacksell U; *J. Med. Chem.* 1997 40 3804–3819] describe the synthesis of certain quinuclidine-2-ene derivatives useful as muscarinic antagonists.

Recently, however, an interest in the development of nicotinic acetylcholine receptor modulators has emerged. Several diseases are associated with degeneration of the cholinergic system, i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision of new quinuclidine derivatives that are modulators of the nicotinic and/or of the monoamine receptors, and which modulators are useful for the treatment of diseases or disorders related to the cholinergic receptors, and in particular the nicotinic acetylcholine receptor, the monoamine receptors 5-HTR, DAR and NER, and the biogenic amine transporters for 5-HT, DA and NE.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

Accordingly, in its first aspect the invention provides 3-substituted quinuclidine derivatives represented by the general Formula I

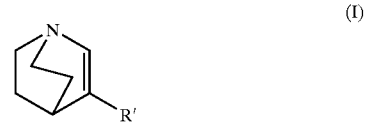

wherein

- - - - represents an optional double bond; and

R' represents a bicyclic carbocyclic or a bicyclic heterocyclic group other than benzo[b]furanyl, 2,3-dihydrobenzo[b]furanyl, benzo[b]thienyl, benzoxazolyl, benzothiazolyl and 2-furo[3,2-b]pyridinyl, which carbocyclic or heterocyclic group is optionally substituted one or more times with alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl;

any of its enantiomers or any mixture of enantiomers, or a pharmaceutically acceptable salt thereof.

In a second aspect the invention provides pharmaceutical compositions comprising a therapeutically effective amount of a 3-substituted quinuclidine derivative of the invention, or a pharmaceutically acceptable addition salt thereof, together with at least one pharmaceutically acceptable carrier or diluent.

Viewed from another aspect the invention relates to the use of a 3-substituted quinuclidine derivative of the invention for the treatment, prevention or alleviation of a disease or a disorder or a condition that is responsive to the action of a nicotinic acetylcholine receptor modulator.

In yet another aspect the invention provides a method of the treatment or alleviation of a disease or disorder of a living animal body, including a human, which disease or disorder is responsive to the action of a nicotinic acetylcholine receptor modulator, which method comprises the step of administering to such a living animal body, including a human, in need thereof a therapeutically effective amount of the 3-substituted quinuclidine derivative of the invention.

Other objects of the invention will be apparent to the person skilled in the art from the following detailed description and examples.

DETAILED DISCLOSURE OF THE INVENTION

3-Substituted Quinuclidine Derivatives

In its first aspect the invention provides novel 3-substituted quinuclidine derivatives represented by the general Formula I

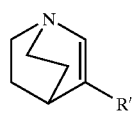

(I)

wherein

- - - - represents an optional double bond; and

R' represents a bicyclic carbocyclic or a bicyclic heterocyclic group other than benzo[b]furanyl, 2,3-dihydro-benzo[b]furanyl, benzo[b]thienyl, benzoxazolyl, benzothiazolyl and 2-furo[3,2-b]pyridinyl, which carbocyclic or heterocyclic group is optionally substituted one or more times with alkyl, alkoxy, alkoxyalkyl, cycloalkyl, cycloalkoxy, alkoxycycloalkyl, cycloalkoxyalkyl, cycloalkylalkyl, hydroxyalkyl, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl;

any of its enantiomers or any mixture of enantiomers, or a pharmaceutically acceptable salt thereof.

In a preferred embodiment the 3-substituted quinuclidine derivative of the invention is represented by the general Formula II

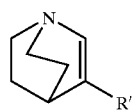

(II)

wherein R' represents a bicyclic carbocyclic or a bicyclic heterocyclic group other than benzo[b]furanyl, benzo[b]thienyl, benzoxazolyl, benzothiazolyl and 2-furo[3,2-b]pyridinyl, which carbocyclic or heterocyclic group is optionally substituted one or more times with alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In another preferred embodiment the 3-substituted quinuclidine derivative of the invention is represented by the general Formula III

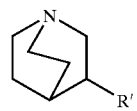

(III)

wherein R' represents a bicyclic carbocyclic or a bicyclic heterocyclic group other than benzo[b]furanyl and 2,3-dihydro-benzo[b]furanyl, which carbocyclic or heterocyclic group is optionally substituted one or more times with alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

The bicyclic carbocyclic group of the invention preferably is an aromatic or partially saturated hydrocarbon group, i.e. a bicyclic aryl group. Examples of preferred bicyclic aryl groups of the invention include indenyl, naphthyl and azulenyl.

In a most preferred embodiment, the bicyclic carbocyclic group is indenyl or naphthyl.

The bicyclic heterocyclic group of the invention holds one or more heteroatoms in its ring structure. Preferred heteroatoms include nitrogen (N), oxygen (O), and sulphur (S).

Preferred bicyclic heterocyclic groups of the invention include 5- and 6 membered rings. The ring structures may in particular be aromatic or partially saturated (i.e. a heteroaryl).

In a more preferred embodiment, the bicyclic heterocyclic group is benzimidazolyl, in particular 2,5 or 6-benzimidazolyl; cinnolinyl, in particular 6 or 7-cinnolinyl; 1H-indazolyl, in particular 1H-indazol-2,5 or 6-yl; indolyl, in particular 2,5 or 6-indolyl; isoindolyl, in particular 2,5 or 6-isoindolyl; 3H-indolyl, in particular 3H-indol2,5 or 6-yl; indolinyl, in particular 2,5 or 6-indolinyl; indolizinyl, in particular 2,5 or 6-indolizinyl; 1,5-naphthyridinyl, in particular 1,5-naphthyridin-2,3,6 or 7-yl; 1,8-naphthyridinyl, in particular 1,8-naphthyridin-2,3,6 or 7-yl; phthalazinyl, in particular 6 or 7-phthalazinyl; purinyl, in particular 2 or 8-purinyl; pteridinyl, in particular 2,6 or 7-pteridinyl;

quinolinyl, in particular 2,3,6 or 7-quinolinyl; isoquinolinyl, in particular 3,6 or 7-isoquinolinyl; quinazolinyl, in particular 2,6 or 7-quinazolinyl; 4H-quinolizinyl, in particular 4H-quinolizin-2,3,7 or 8-yl; or quinoxalinyl, in particular 2 or 6-quinoxalinyl.

In its most preferred embodiment, the quinuclidine derivative of the invention is 3-(2-Naphthyl)-quinuclidine-3-ene;
(±)-3-(2-Naphthyl)-quinuclidine;
3-(2-Quinolinyl)-quinuclidine-3-ene;
(±)-3-(2-Quinolinyl)-quinuclidine;
3-(3-Quinolinyl)-quinuclidine-3-ene;
(±)-3-(3-Quinolinyl)-quinuclidine;
3-(3-Isoquinolinyl)-quinuclidine-3-ene;
(±)-3-(3-Isoquinolinyl)-quinuclidine;
(±)-3-(2-Benzothiazolyl)-quinuclidine;
3-(2-Benzo[b]thienyl)-quinuclidine-3-ene;
(±)-3-(2-Benzo[b]thienyl)-quinuclidine;
3-(2-Indolizinyl)-quinuclidine-3-ene;
(±)-3-(2-Indolizinyl)-quinuclidine;
3-(1-Methyl-2-indolyl)-quinuclidine-3-ene;
(±)-3-(1-Methyl-2-indolyl)-quinuclidine;
3-(2-Quinoxalinyl)-quinuclidine-3-ene;
(±)-3-(2-Quinoxalinyl)-quinuclidine;
3-(2-Quinazolinyl)-quinuclidine-3-ene;
(±)-3-(2-Quinazolinyl)-quinuclidine;
3-[2-(1,8-Naphthyridinyl]-quinuclidine-3-ene;
(±)-3-[2-(1,8-Naphthyridinyl]-quinuclidine;
3-[2-(1,5-Naphthyridinyl]-quinuclidine-3-ene; or
(±)-3-[2-(1,5-Naphthyridinyl]-quinuclidine;

any of its enantiomers or any mixture of enantiomers, or a pharmaceutically acceptable salt thereof.

Definition of Substituents

In the context of this invention halogen represents fluorine, chlorine, bromine or iodine.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butynyl; 1-, 2-, 3-, 4-pentynyl, or 1,3-pentynyl; 1-, 2-, 3-, 4-, or 5-henynyl, or 1,3-hexynyl or 1,3,5-hexynyl; 1-, 2-, 3-, 4-, 5- or 6-heptynyl, or 1,3-heptynyl, or 1,3,5-heptynyl; 1-, 2-, 3-, 4-, 5-, 6- or 7-octynyl, or 1,3-octynyl, or 1,3,5-octynyl, or 1,3,5,7-octynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above, an alkenoxy group designates an "alkenyl-O—" group, wherein alkenyl is as defined above, an alkynoxy group designates an "alkynyl-O—" group, wherein alkynyl is as defined above, an alkoxyalkyl group designates an "alkyl-O-alkyl" group, wherein alkyl is as defined above, an alkoxyalkenyl group designates an "alkyl-O-alkenyl" group, wherein alkyl and alkenyl are as defined above, an alkoxyalkynyl group designates an "alkyl-O-alkynyl" group, wherein alkyl and alkynyl are as defined above, a cycloalkoxy group designates a "cycloalkyl-O-" group, wherein cycloalkyl is as defined above, a alkoxycycloalkyl group designates a "alkyl-O-cycloalkyl-" group, wherein alkyl and cycloalkyl are as defined above, and a cycloalkoxyalkoxy group designates a "cycloalkyl-O-alkyl-O—" group, wherein alkyl and cycloalkyl are as defined above.

In the context of this invention an alkylthio group designates an "alkyl-S—" group (thioalkoxy), wherein alkyl is as defined above, an alkenylthio group designates an "alkenyl-S—" group, wherein alkenyl is as defined above, and an alkynylthio group designates an "alkynyl-S—" group, wherein alkynyl is as defined above.

In the context of this invention an alkylseleno group designates an "alkyl-Se—" group, wherein alkyl is as defined above, an alkenylseleno designates an "alkenyl-Se—" group, wherein alkenyl is as defined above, and an alkynylseleno group designates an "alkynyl-Se—" group, wherein alkynyl is as defined above.

In the context of this invention an alkyloxime group designates a "C=N—O-alkyl" group, wherein alkyl is as defined above, and an acyloxime group designates a "C=N—O—COOH" group or a "C=N—O—CO-alkyl" group, wherein alkyl is as defined above.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aralkyl group designates an aryl group as defined above, which aryl group is attached to an alkyl group as also defined above. Examples of preferred aralkyl groups of the invention include benzyl.

In the context of this invention a bicyclic carbocyclic group is a bicyclic compound holding carbon only as ring atom. The ring structure may in particular be aromatic (i.e. an aryl group), or saturated or partially saturated. Preferred bicyclic carbocyclic groups of the invention include 5- and 6 membered bicyclic carbocyclic groups. Most preferred bicyclic carbocyclic groups of the invention are the aromatic bicyclic groups and include indanyl, naphthalenyl, azulenyl.

In the context of this invention a bicyclic heterocyclic group is a bicyclic compound, which holds one or more heteroatoms in its ring structure. Preferred heteroatoms include nitrogen (N), oxygen (O), and sulphur (S). The ring structure may in particular be aromatic (i.e. a heteroaryl), or saturated or partially saturated. Preferred bicyclic heterocyclic groups of the invention include 5- and 6 membered bicyclic heterocyclic groups.

In a more preferred embodiment, the bicyclic heterocyclic group is benzimidazolyl, in particular 2,5 or 6-benzimidazolyl;

cinnolinyl, in particular 6 or 7-cinnolinyl;

1H-indazolyl, in particular 1H-indazol-2,5 or 6-yl;

indolyl, in particular 2,5 or 6-indolyl;

isoindolyl, in particular 2,5 or 6-isoindolyl;

3H-indolyl, in particular 3H-indol-2,5 or 6-yl;

indolinyl, in particular 2,5 or 6-indolinyl;

indolizinyl, in particular 2,5 or 6-indolizinyl;

1,5-naphthyridinyl, in particular 1,5-naphthyridin-2,3,6 or 7-yl;

1,8-naphthyridinyl, in particular 1,8-naphthyridin-2,3,6 or 7-yl;

phthalazinyl, in particular 6 or 7-phthalazinyl;

purinyl, in particular 2 or 8-purinyl;

pteridinyl, in particular 2,6 or 7-pteridinyl;

quinolinyl, in particular 2,3,6 or 7-quinolinyl;

isoquinolinyl, in particular 3,6 or 7-isoquinolinyl;

quinazolinyl, in particular 2,6 or 7-quinazolinyl;

4H-quinolizinyl, in particular 4H-quinolizin-2,3,7 or 8-yl; or quinoxalinyl, in particular 2 or 6-quinoxalinyl.

Pharmaceutically Acceptable Salts

The 3-substituted quinuclidine derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

Steric Isomers

The 3-substituted quinuclidine derivatives of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or I- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J. Collet A, & Wilen S in *"Enantiomers, Racemates, and Resolutions"*, John Wiley and Sons, New York (1981).

Optical active compounds can also be prepared from optical active starting materials.

Methods of Preparation

The 3-substituted quinuclidine derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The 3-substituted quinuclidine derivatives of the present invention are found to be cholinergic ligands at the nicotinic acetylcholine receptors, and modulators of the monoamine receptors, in particular the biogenic amine transporters 5-HT, DA and NE. Also preferred diazabicycloalkane derivatives of the invention show selective $\alpha_7$ activity.

In the context of this invention the term "modulator" covers agonists, partial agonists, antagonists and allosteric modulators of the receptor.

Nicotinic acetylcholine receptors in the brain are pentameric structures composed of subunits distinct from those found in skeletal muscles. The existence of seven $\alpha$-subunits ($\alpha_2$–$\alpha_7$, $\alpha_9$) and three $\beta$-subunits ($\beta_2$–$\beta_4$) in the mammalian brain has been described. The predominant subtype with high affinity for nicotine is comprised of $\alpha_4$ and $\beta_2$ subunits.

The compounds of the present invention may in particular be characterised by having a high binding activity for the $\alpha_7$ subtype.

The affinity of compounds of the invention for nicotinic acetylcholine receptors may be investigated using standard assays, e.g.

the in vitro inhibition of $^3$H-epibatidin binding, which is a standard assay for determining non-selective binding to nicotinic receptors, the in vitro inhibition $^3$H-cytisine binding, which is a standard assay for determining selective binding to $\alpha_4\beta_2$ subtype of nicotinic receptors, and/or the in vitro inhibition of $^3$H-α-bungarotoxin binding, which is a standard assay for determining selective binding to $\alpha_7$ subtype of nicotinic receptors.

Such standard assays are described in e.g. WO 99/21834.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, premenstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

Neuroimaging

The 3-substituted quinuclidine derivatives of the invention may be useful as diagnostic tools or monitoring agents in various diagnostic methods, and in particular for in vivo receptor imaging (neuroimaging).

In another aspect of the invention a method for the non-invasive determination of the distribution of a tracer compound inside a whole, intact living animal or human body using a physical detection method is provided. According to this method a tracer compound is a compound of the invention, or any of its enantiomers or any mixture thereof, or a pharmaceutically acceptable salt thereof, in labelled or unlabelled form.

In a preferred embodiment the physical detection method is selected from PET, SPECT, MRS, MRI, CAT, or combinations thereof.

The compounds of the invention may be used in their labelled or unlabelled form. In the context of this invention "label" stands for the binding of a marker to the compound of interest that will allow easy quantitative detection of said compound.

The labelled compound of the invention preferably contains at least one radionuclide as a label. Positron emitting radionuclides are all candidates for usage. In the context of this invention the radionuclide is preferably selected from $^{11}$C, $^{18}$F, $^{15}$O, $^{13}$N, $^{123}$I, $^{125}$I, $^{131}$I, $^{3}$H and $^{99m}$Tc.

An examples of commercially available labelling agents, which can be used in the preparation of the labelled compounds of the present invention is [$^{11}$C]$O_2$, $^{18}$F, and NaI with different isotopes of Iodine.

In particular [$C^{11}$]$O_2$ may be converted to a [$^{11}$C]-methylating agent, such as [$^{11}$C]$H_3$I or [$^{11}$C]-methyl triflate.

Labelled compounds containing e.g. [$^{125}$I] labelled 1-iodoprop-1-en-3-yl as substituent on N-8 may be prepared as described in the art [Elmaleh, et al.; *J. Nucl. Med.* 1996 37 1197–1202].

Labelled compounds containing e.g. [$^{18}$F]-alkyl substituted N-8 may be prepared as described in the art, e.g. in WO 96/39198.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including deuterium, tritium, $^{13}$C, $^{14}$C, $^{131}$I, $^{125}$I, $^{123}$I, and $^{18}$F, the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diagnostically effective amount of the labelled or unlabelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of a 3-substituted quinuclidine derivatives of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 3-substituted quinuclidine derivatives of the invention, or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

Methods of Therapy

The compounds of the present invention are valuable nicotinic acetylcholine receptor modulators and therefore useful for the treatment of a range of ailments involving cholinergic dysfunction as well as a range of disorders responsive to the action of nicotinic acetylcholine receptor modulators as well as the serotonin receptor.

In another aspect the invention relates to the a method of the treatment or alleviation of a disease, disorder or condition of a living animal body, including a human, which disease, disorder or condition is responsive to the action of a nicotinic acetylcholine receptor modulator, which method comprises the step of administering to such a living animal body, including a human, in need thereof a therapeutically effective amount of the chemical compound of the invention.

In the context of this invention the term "treating" covers treatment, prevention, prophylaxis or alleviation, and the term "disease" covers illnesses, diseases, disorders and conditions related to the disease in question.

In a preferred embodiment the disease or disorder to be treated is a disease or disorder of the central nervous system, a disease or disorder caused by or related to smooth muscle contraction, an endocrine disorder, a disease or disorder caused by or related to neuro-degeneration, a disease or disorder caused by or related to inflammation, pain, a withdrawal symptom caused by the termination of abuse of chemical substances.

In a more preferred embodiment the disease or disorder of the central nervous system is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourettes syndrome, depression, mania, manic depression, schizophrenia, obsessive compulsive disorders (OCD), panic disorders, eating disorders such as anorexia nervosa, bulimia and obesity, narcolepsy, nociception, dementia, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, premenstrual syndrome, late luteal phase syndrome, chronic fatigue syndrome, mutism, trichotillomania, and jet-lag.

In another preferred embodiment the disease or disorder caused by or related to smooth muscle contraction are convulsive disorders, angina pectoris, premature labour, convulsions, diarrhoea, asthma, epilepsy, tardive dyskinesia, hyperkinesia, premature ejaculation, and erectile difficulty.

In a third preferred embodiment the endocrine disorder is thyrotoxicosis, pheochromocytoma, hypertension and arrhythmias.

In a fourth preferred embodiment the neuro-degenerative disease is transient anoxia and induced neurodegeneration.

In a fifth preferred embodiment the disease or disorder caused by or related to inflammation is an inflammatory skin disorder such as acne and rosacea, Chron's disease, inflammatory bowel disease, ulcerative colitis, and diarrhoea.

In a sixth preferred embodiment pain is a mild, a moderate or a severe pain of acute, chronic or recurrent character, a pain caused by migraine, a postoperative pain, or a phantom limb pain.

In a third preferred embodiment the addictive substance is a nicotine containing product such as tobacco, an opioids such as heroin, cocaine or morphine, a benzodiazepine or a benzodiazepin-like drug, or alcohol.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

General: All reactions involving air sensitive reagents or intermediates were performed under nitrogen and in anhydrous solvents. Magnesium sulphate was used as drying agent in the workup-procedures and solvents were evaporated under reduced pressure.

Method A (±)-3-(2-Naphthyl)-quinuclidine-3-ol (Compound A1)

Butyllithium (31 ml, 72 mmol) was added to a mixture of 2-bromonaphthalene (14.9 g, 72.1 mmol) and diethyl ether (300 ml) at −70° C. The resulting mixture was stirred at −70° C. for 30 minutes. A mixture of 3-quinuclidinone and diethyl ether (150 ml) was added at −70° C. The mixture was stirred at −70° C. for 1 hour and was then allowed to reach room temperature. Aqueous sodium hydroxide (400 ml, 1 M) was added. The phases were separated and the aqueous phase was extracted with diethyl ether (100 ml). The combined organic phases were purified by chromatography on silica gel with dichloromethane, methanol and conc. ammonia (89:10:1) gave the title compound. Yield 2.03 g (11%).

Method B 3-(2-Naphthyl)-quinuclidine-3-ene fumaric acid salt (Compound B1)

3-(2-Naphthyl)-quinuclidine-3-ol (2.0 g, 7.9 mmol) and hydrochloric acid (60 ml, 25%) was stirred at reflux overnight. The reaction-mixture was evaporated and aqueous sodium hydroxide (50 ml, 4 M) was added. The mixture was extracted with ethyl acetate (3×30 ml). The combined organic phases were purified by chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 0.89 g (32%). Mp. 223–229° C.

Method C (±)-3-(2-Naphthyl)-quinuclidine fumaric acid salt (Compound C1)

3-(2-Naphthyl)-quinuclidine-3-ene (0.40 g, 1.9 mmol), palladium on carbon (200 mg, 10%), tetrahydrofuran (90 ml), ethanol (10 ml) and concentrated hydrochloric acid (0.1 ml) was stirred under hydrogen for 2 days. The crude mixture was filtered through celite. The corresponding salt was obtained by addition of a diethyl ether and methanol mixture (9:1) saturated with fumaric acid. Yield 0.18 g (27%). Mp. 168.1–170.8° C.

The following compounds are prepared according to Method C:

3-(2-Quinolinyl)-quinuclidine-3-ene;
(±)-3-(2-Quinolinyl)-quinuclidine;
3-(3-Quinolinyl)-quinuclidine-3-ene;
(±)-3-(3-Quinolinyl)-quinuclidine;
3-(3-Isoquinolinyl)-quinuclidine-3-ene;
(±)-3-(3-Isoquinolinyl)-quinuclidine;
3-(2-Benzothiazolyl)-quinuclidine-3-ene;
(±)-3-(2-Benzothiazolyl)-quinuclidine;
3-(2-Benzo[b]thienyl)-quinuclidine-3-ene;
(±)-3-(2-Benzo[b]thienyl)-quinuclidine;
3-(2-Indolizinyl)-quinuclidine-3-ene;
(±)-3-(2-Indolizinyl)-quinuclidine;
3-(1-Methyl-2-indolyl)-quinuclidine-3-ene;
(±)-3-(1-Methyl-2-indolyl)-quinuclidine;
3-(2-Quinoxalinyl)-quinuclidine-3-ene;
(±)-3-(2-Quinoxalinyl)-quinuclidine;
3-(2-Quinazolinyl)-quinuclidine-3-ene;
(±)-3-(2-Quinazolinyl)-quinuclidine;
3-[2-(1,8-Naphthyridinyl]-quinuclidine-3-ene;
(±)-3-[2-(1,8-Naphthyridinyl]-quinuclidine;
3-[2-(1,5-Naphthyridinyl]-quinuclidine-3-ene; and
(±)-3-[2-(1,5-Naphthyridinyl]-quinuclidine.

Example 2

Biological Activity

In this example the affinity of compounds of the invention for nicotinic acetylcholine receptors are investigated using standard assays described in WO 99/21834.

First the in vitro inhibition of $^3$H-epibatidin binding, which is a standard assay for determining non-selective binding to nicotinic receptors, was determined.

Next the in vitro inhibition $^3$H-cytisine binding, which is a standard assay for determining selective binding to $\alpha_4\beta_2$-subtype of nicotinic receptors, was determined.

Finally the in vitro inhibition of $^3$H-α-bungarotoxin binding, which is a standard assay for determining selective binding to $\alpha_7$-subtype of nicotinic receptors, was determined.

The results of these determinations are presented in Table 1 below.

TABLE 1

| | in vitro Inhibition of Binding (IC$_{50}$) | | |
|---|---|---|---|
| Compound | $^3$H-epibatidin binding | $^3$H-cytisine binding | $^3$H-α-bungarotoxin binding |
| B1 | 17 μM | 10 μM | 0.058 μM |
| C1 | 7.5 μM | 6 μM | 0.15 μM |

These data clearly shows the selectivity of the compounds of the invention for the $\alpha_7$-subtype of nicotinic receptors.

What is claimed is:

1. A 3-substituted quinuclidine compound represented by Formula I

wherein

- - - - represents an optional double bond; and

R' represents a bicyclic carbocyclic group which bicyclic carbocyclic group is optionally substituted one or more times with substituents selected from the group consisting of alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, a group of the formula —(CO)R$^3$, —COOR$^3$, —O(CO)R$^3$, —CONR$^2$R$^3$, —NH—CO$_2$R$^2$, —NHCO—R$^2$ and —OCO—NR$^2$R$^3$; in which formulas R$^2$ and R$^3$ independently of each another represents hydrogen or alkyl;

any of its enantiomers or any mixture of enantiomers, or a pharmaceutically acceptable salt thereof.

2. The quinuclidine compound of claim 1, wherein the bicyclic carbocyclic group is indenyl or naphthyl.

3. The quinuclidine compound of claim 2, which is 3-(2-Naphthyl)-quinuclidine-3-ene; or (±)-3-(2-Naphthyl)-quinuclidine;

any of its enantiomers or any mixture of enantiomers, or a pharmaceutically acceptable salt thereof.

4. A pharmaceutical composition comprising a therapeutically effective amount of a 3-substituted quinuclidine compound of claim 1, any of its enantiomers or any mixture of enantiomers, or a pharmaceutically acceptable salt thereof, together with at least one pharmaceutically acceptable carrier or diluent.

* * * * *